US010078204B2

(12) United States Patent
Ghosh et al.

(10) Patent No.: US 10,078,204 B2
(45) Date of Patent: Sep. 18, 2018

(54) NON-DESTRUCTIVE 3-DIMENSIONAL CHEMICAL IMAGING OF PHOTO-RESIST MATERIAL

(71) Applicant: Intel Corporation, Santa Clara, CA (US)

(72) Inventors: Nilanjan Z. Ghosh, Chandler, AZ (US); Kevin T. McCarthy, Tempe, AZ (US); Zhiyong Wang, Chandler, AZ (US); Deepak Goyal, Phoenix, AZ (US); Changhua Liu, Chandler, AZ (US); Leonel R. Arana, Phoenix, AZ (US)

(73) Assignee: Intel Corporation, Santa Clara, CA (US)

( * ) Notice: Subject to any disclaimer, the term of this patent is extended or adjusted under 35 U.S.C. 154(b) by 399 days.

(21) Appl. No.: 14/229,909

(22) Filed: Mar. 29, 2014

(65) Prior Publication Data

US 2015/0276480 A1 Oct. 1, 2015

(51) Int. Cl.
*G01J 3/28* (2006.01)
*G01J 3/04* (2006.01)
(Continued)

(52) U.S. Cl.
CPC .......... *G02B 21/008* (2013.01); *G01N 21/65* (2013.01); *G01N 21/8422* (2013.01);
(Continued)

(58) Field of Classification Search
None
See application file for complete search history.

(56) References Cited

U.S. PATENT DOCUMENTS 5,329,352 A * 7/1994 Jacobsen .................. G01J 3/02
356/301
2006/0286811 A1* 12/2006 Heiden .............. G01N 21/6456
438/759

(Continued)

OTHER PUBLICATIONS

Gierlinger et al, "Chemical Imaging of Poplar Wood Cell Walls by Confocal Raman Microscopy", Plant Physiology, Apr. 2006, vol. 140, pp. 1246-1254.*

(Continued)

*Primary Examiner* — Dominic J Bologna
(74) *Attorney, Agent, or Firm* — Schwabe, Williamson & Wyatt, P.C.

(57) ABSTRACT

Embodiments include devices, systems and processes for using a combined confocal Raman microscope for inspecting a photo resist film material layer formed on the top surface of a layer of a substrate package, to detect border defects between regions of light exposed (e.g., cured) and unexposed (e.g., uncured) resist film material. Use of the confocal Raman microscope may provide a 3D photo-resist chemical imaging and characterization technique based on combining (1) Raman spectroscopy to identify the borders between regions of light exposed and unexposed resist along XY planes, with (2) Confocal imaging to select a Z-height of the XY planes scanned. Such detection provides fast, high resolution, non-destructive in-line inspection, and improves technical development of polymerization profiles of the resist film material.

36 Claims, 6 Drawing Sheets

(51) Int. Cl.
  *G01J 3/44*    (2006.01)
  *G02B 21/00*   (2006.01)
  *G01N 21/65*   (2006.01)
  *G01N 21/84*   (2006.01)
  *G01N 21/95*   (2006.01)
  *G01N 21/21*   (2006.01)

(52) U.S. Cl.
  CPC ..... *G01N 21/9501* (2013.01); *G02B 21/0064* (2013.01); *G01J 3/44* (2013.01); *G01N 21/21* (2013.01); *G01N 2021/656* (2013.01)

(56) References Cited

U.S. PATENT DOCUMENTS

| | | | | |
|---|---|---|---|---|
| 2008/0286682 A1* | 11/2008 | Yeh | ............... | G03F 7/0397 430/270.1 |
| 2009/0189630 A1* | 7/2009 | Ippolito | ............... | G01R 31/311 324/754.23 |
| 2010/0241357 A1* | 9/2010 | Chan | ............... | G01J 3/44 702/19 |
| 2012/0314206 A1* | 12/2012 | Spizig | ............... | G02B 21/006 356/72 |
| 2014/0272677 A1* | 9/2014 | Raghunathan | ............... | G03F 7/2022 430/5 |

OTHER PUBLICATIONS

Intel Research and Development "Virtual Press Kit" Apr. 25, 2008, available at "https://web.archive.org/web/20080425182736/http://www.intel.com/pressroom/archive/backgrnd/20011008tech_bkgrd.htm".*

* cited by examiner

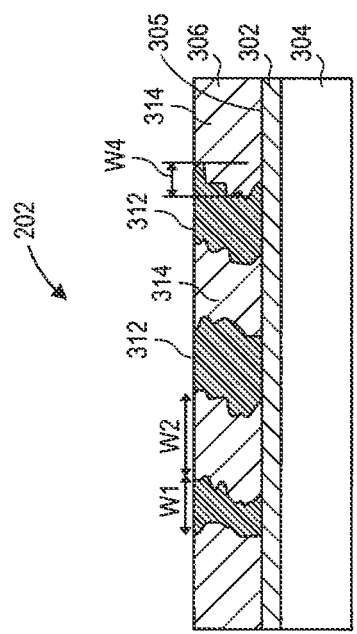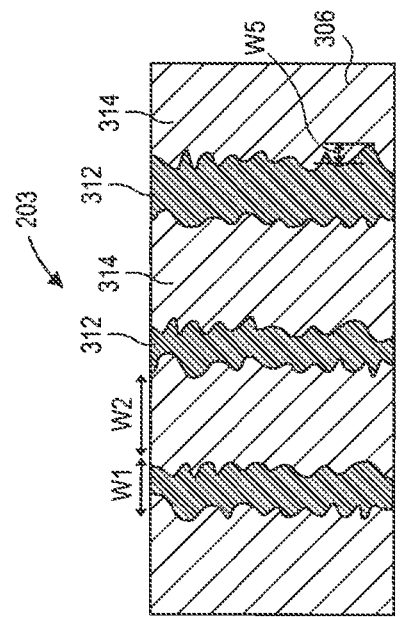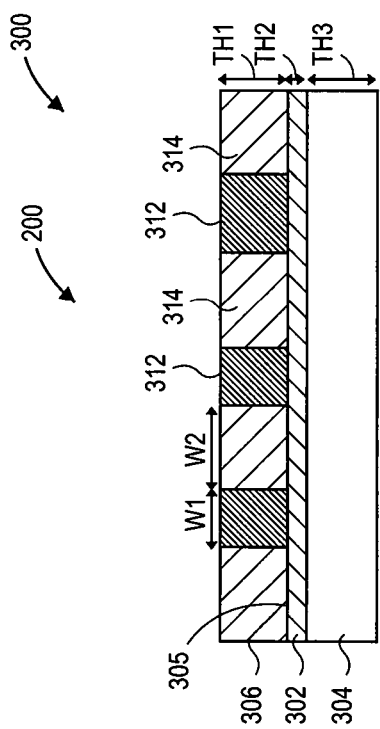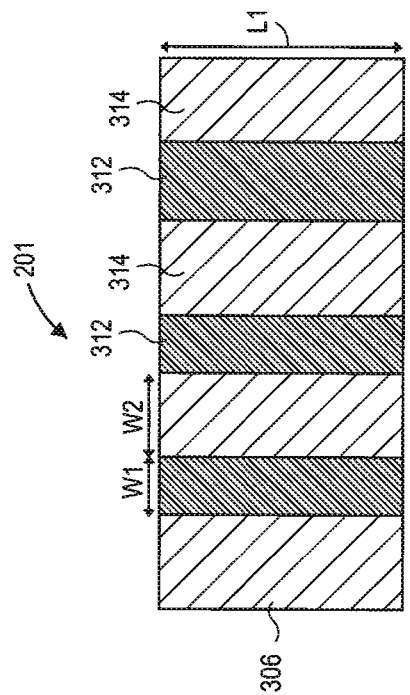
FIG. 2A
FIG. 2B
FIG. 2C
FIG. 2D

NON-DESTRUCTIVE 3-DIMENSIONAL CHEMICAL IMAGING OF PHOTO-RESIST MATERIAL

BACKGROUND

Field

Embodiments of the invention are related to inspecting a photo resist film material layer, such as formed on the top surface of a conductive layer of a chip package, to detect border defects between regions of light exposed (e.g., cured) and unexposed (e.g., uncured) resist film material.

Description of Related Art

One of the key issues resulting in high yield loss in substrate package technology development (SPTD) or bump-less build-up layer (BBUL) packaging is unacceptable borders or defective borders (e.g., "border defects") between regions of light exposed (e.g., cured) and unexposed (e.g., uncured) resist film material.

Currently no solutions exist in the industry for 3-Dimensional (3D) imaging and quantitative characterization of photo-resist during or after exposure to light to cure the material, such as to identify border defects. This greatly limits process development and optimization for substrate technology development. Inconsistencies or defects in the exposure lighting, or mask used to expose the exposed regions may be contributors for border defects "hidden defects". Such defects can include dry film resist (DFR) border defects of film patterned onto electroless conductor (e.g., copper) to form conductive traces (e.g., copper traces) on an insulating layer or on a package substrate.

Such defects can result in inaccurate or unacceptable trace geometry, and thus cause conductive traces to malfunction, short to other traces, or open circuit where contact should exist. Such defects also can result in smaller contact area between conductive traces and insulating substrate, and thus cause conductive trace to lift off in downstream process. Such liftoff can result in damaged, destroyed or missing lengths of the conductive traces, often causing undesired open circuits in the trace circuitry.

Therefore, it is desirable to provide imaging and quantitative characterization of photo-resist during or after exposure to light to cure the material, such as to identify border defects.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one.

FIG. 2A-D show schematic views and profiles of unexposed 3D regions of a photo resist layer, and exposed 3D regions of the photo resist layer.

DETAILED DESCRIPTION

Figure 1A:
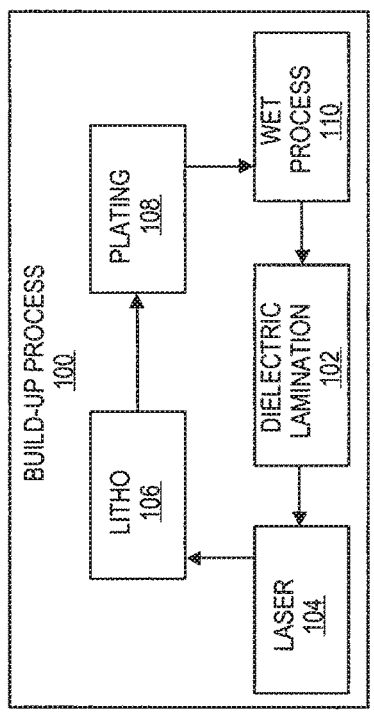
FIG. 1A is a block diagram a build-up process for building up layers of a substrate package, according to some embodiments.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

Embodiments of the invention provide devices, systems and processes for using a combined confocal Raman microscope for inspecting (e.g., monitoring, detecting or imaging) a photo resist film material layer formed on the top surface of a layer of a substrate package to detect (e.g., distinguish or identify) border defects between regions of light exposed (e.g., cured) and unexposed (e.g., uncured) resist film material. Such as confocal Raman microscope may include or use a confocal Raman microspectromete; or a Raman spectroscopy combined with a confocal microscopy device for inspecting the resist to detect the defects.

Use of the confocal Raman microscope may provide a 3D photo-resist chemical imaging and characterization technique based on combining (1) Raman spectroscopy to identify, map or detect the border between regions of light exposed and unexposed resist film along horizontal or XY planes, with (2) Confocal imaging to select a vertical height or Z-height for the XY planes scanned with Raman spectroscopy. Such detection may identify such defects by detecting unacceptable borders or border width of borders between regions of light exposed and unexposed resist film material. By detecting the defects, it is possible to determine or improve the trace quality, tight fine line spacing, curing profile, under-over development profile, exposed-unexposed profile, and/or polymerization profile of the resist film material (e.g., of light exposed (e.g., cured) and unexposed (e.g., uncured) resist film material).

Embodiments of the invention provide several advantages or benefits. Embodiments, of the current invention provide fast (e.g., in minutes), high resolution (resolution <1 um), non-destructive, 3-dimensional (3D) chemical imaging of photo-resist possible in an in-line setting. Thus, embodiments enable in-line process control to monitor in three-dimensions, the trace quality as shown in FIG. 2 below and optimize technical design (TD) process (such as process design for performing such light exposure) to achieve very tight fine line spacing through direct 3D imaging feedback. Such technical development may include processes for manufacturing or building substrate packages for electronic device packaging.

FIG. 1A is a block diagram a build-up process for building up layers of a substrate package, according to some embodiments. FIG. 1A shows process 100, such as for a build-up process for building up layers 302, 304 and 306 of a substrate package as shown below. The process may be a circular process 100. Process 100 starts at block 102 where a top surface of an insulator or dielectric layer, a substrate, or conductor layer is laminated with a dielectric or insulator layer.

At block 104 the dielectric lamination is etched with a laser, such as to form openings in the dielectric layer. In some cases, block 104 includes forming opening into or through the dielectric or the dielectric and other layers (e.g., such as to form through silicon vias (TSV) into or through the substrate). In some cases, block 104 is or includes a key lithographic and/or patterning process where the electronic circuitry is laid out.

At block 106 the etched dielectric layer is lithographically patterned and etched, such as by laminating a photo resist film layer on the dielectric layer and patterning and etching the resist to form openings (e.g. see FIG. 2). In some cases, block 106 is described further below, and/or in FIG. 1B.

At block 108 conductor (e.g., electro plated copper) is plated into the openings formed in or through the resist layer. In some cases, block 108 includes electro plating a conductor (e.g., copper) onto exposed electroless platings of conductor (e.g., copper) that are exposed through openings in a photo resist which are formed at block 106.

For example, a plating module or processing chamber may have or be able to perform two different plating processes. In the first process, the module plates a dielectric substrate surface (e.g., see block 102 and layer 304) with an electroless conductor (e.g., see block 106 and layer 302).

Then, in the second process, the module plates the electroless conductor surface (e.g., see block 108 and surface 305) with an electro plated conductor (e.g., to form conductive traces and/or contacts by electro plating a conductor (e.g., copper) onto exposed electroless platings of conductor (e.g., copper) that are exposed through openings in a photo resist (e.g., where unexposed photo resist 3D regions 314 are removed from layer 306) which are formed at block 106.

In some cases, in the first process, a dielectric substrate surface (e.g., see block 102 and layer 304) is electrolessly plated with an electroless conductor (e.g., see block 106 and layer 302). Then, the top surface of the electroless conductor is laminated with a dry film photo resist. Then, a laser exposure and development process is performed (e.g., to pattern openings through the resist, including openings where unexposed regions 314 are removed or patterned). Then, conductor is plated again to form or fill up where regions 314 were removed to form conductor patterns for trances and/or contacts. These conductor patterns may be electro plated (e.g., not electroless) onto the electroless conductor surface (e.g., seed layer).

In other embodiments or descriptions, electroless layer 302 is not present or is not described. Here, layer 306 may be laminated upon or described as laminated upon a top surface of insulating layer 304.

Then, at block 110, a wet process is used to remove remaining resist (e.g., regions 312 of layer 306) so that the conductive plating forms conductive traces and/or contacts on the dielectric lamination. These conductive traces and/or contacts may include conductive traces and/or contacts to TSV conductors or connections extending through the substrate.

Figure 1B:
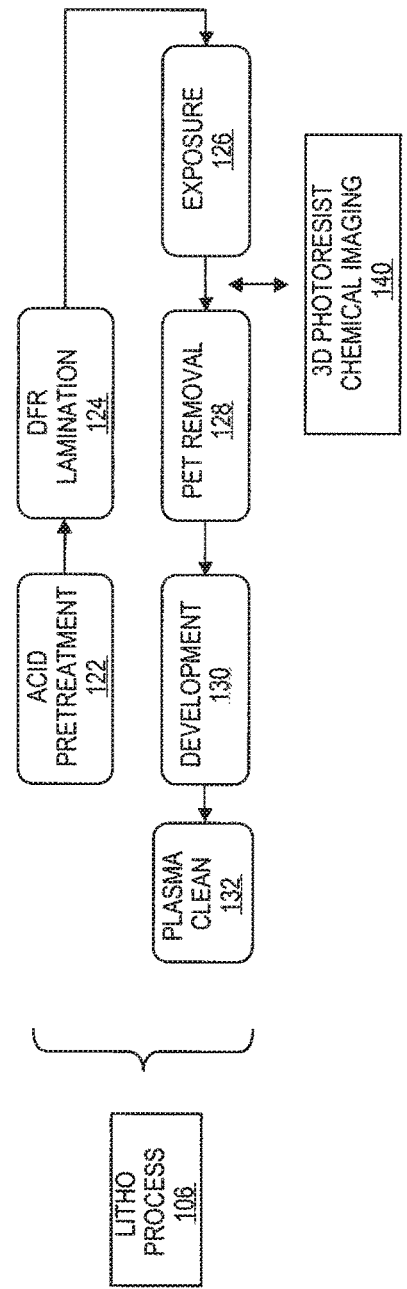
FIG. 1B shows lithographic process of FIG. 1A.

FIG. 1B shows lithographic process 106 of FIG. 1A. After laser etching at block 104, process 106 continues at block 122 with acid pretreatment of the laser-etched surface of the dielectric lamination. Then at block 124 photo resist film layer is laminated onto the acid pretreated surface of the dielectric. Such a photo resist film layer may be a lithographic resist film, a resist film material, a photo resist, or a dry film resist (DFR) material layer. Such resist may be or include a polymer, or a thin film polymer.

Then, at block 126, the photo resist film layer is pattern masked and exposed to light to expose some areas (or 3D regions), but not other areas (or 3D regions) of the film. Block 126 shows the exposure of the mask and resist to the UV light. Such exposure to light may expose of the mask and resist to the ultraviolet (UV) light to create light exposed (e.g., cured) and unexposed (e.g., uncured) resist film material (e.g., 3D regions) (e.g. see FIG. 2). Block 126 may include covering the resist lamination with a mask, such as a mask including layers of metal, metal polymer, plastic, or other material that is not transparent; or is mostly (or completely) opaque to ultraviolet light. Block 126 may include exposing the mask covered resist to ultraviolet light to expose or chemically alter areas (or 3D regions) of the resist that are not covered by the mask.

The areas (or 3D regions) that are exposed to the light (e.g., 3D regions 312 below) and will harden or be "cured" when developed, or will undergo chemical reaction or change. For instance, regions 312 of the resist that are not covered by the mask and are exposed to the light will become hardened and will not be dissolved or removed at block 132. The unexposed areas (e.g., 3D regions 314 below) can be patterned or dissolved while the exposed areas remain (e.g., at block 132).

Block 128 shows protective polyester (PET) layer removal. This may include removal of the etch mask (e.g., PET) from the top surface of the resist. In some cases, the PET layer is removed so that the photo resist can be developed and regions removed.

Block 130 shows development of the exposed portions (e.g., regions 312) or areas of the resist, such as to cure or harden them. Block 130 may include developing exposed regions of photo resist (e.g., regions 312), but not developing unexposed regions of photo resist (e.g., regions 314). Block 130 may include opening up patterns in the resist to expose surface 305, which can be filled with plated Cu to form traces, contacts and/or structures that form a basic foundation of the electronic circuit or circuitry of the package substrate.

At block 132, plasma clean is performed to remove the unexposed (e.g., uncured) resist portions or areas (e.g., regions 314). In some cases, block 132 includes cleaning the exposed and unexposed portions of the resist off of layer 304 (and optionally cleaning the electroless layer 302 where it is not electro plated with conductor.

According to embodiments, 3D photo resist chemical imaging process 140 may be performed after exposure at block 126 and prior to PET removal at block 128. In some cases, after block 126 and/or prior to block 128, block 140 uses a combined confocal Raman microscope to inspecting a photo resist film material layer formed on the top surface of a layer of a substrate package to detect (e.g., distinguish or identify) border defects between regions of light exposed (e.g., cured) and unexposed (e.g., uncured) resist film material.

FIG. 2A-D show schematic views and profiles of unexposed 3D regions of a photo resist layer, and exposed 3D regions of the photo resist layer. The exposed 3D regions of the photo resist layer may have been chemically altered to become a polymer, as compared to the unexposed 3D regions of the resist, which remain a monomer. FIGS. 2A-D shows schematic cross-sectional profile 200 (e.g., a vertical or Z-height profile) of unexposed 3D regions 314 of a photo resist layer, and exposed 3D regions 312 of the photo resist layer, having ideal (e.g., acceptable) and bad (e.g., unacceptable for defective) trace quality.

The exposed regions 312 and unexposed regions 314 may each have a width of between 10 and 12 microns (e.g., 1×10-6 meters); and a height of between 25 and 40 microns. In some cases exposed regions 312 represent cured or developed resist material, and unexposed regions 314 represent uncured or undeveloped resist material. There may be defects or inconsistencies in the trace quality, line spacing, curing profile, borders, or interface between the cured and uncured material. These may be due to inconsistencies or defect in the lighting, or mask used to expose the exposed regions.

FIGS. 2A-D show a portion of substrate 300 having conductor surface 305 of conductive layer 302 upon which resist film 306 is laminate or formed. FIGS. 2A-D show substrate 300 having resist layer 306 laminated, coated or formed on top surface 305 of layer 302, which is electrolessly plated or formed on the top surface of insulator layer 304. In some cases, FIGS. 2A-D include laminating a layer of DFR (e.g., layer 306) on an electroless copper surface (e.g., surface 305).

Resist layer 306 may be or include a dry film resist (DFR) material, a photo resist material, an acrylic based polymer material, a visually clear material, a material that is known for use as a resist layer when forming electronic device packages or use as a resist layer used in lithographic patterning to form conductive traces (e.g., block 108). Resist layer 306 may be formed on surface 305 by a process, as described above for block 106 or 124. Resist layer 306 may be formed on surface 305 by a process, such as is known for forming photo resists used in lithographic patterning to form conductive traces. Layer 306 may have thickness TH1 between 5 and 30 microns (e.g., 1×10-6 meters). In some cases, layer 306 may have thickness TH1 between 10 and 15 microns.

In some cases, layer 306 may be or include dry film photo-resist (DFR) as well as solder resist that may be used for SPTD. Such solder resist may be a material similar to DFR but include a silicon oxide filler, and in some cases a coloring (e.g. such as green). Such solder resist may also be described as printed a circuit board (PCB).

Layer 302 may be or include a conductor layer, a conductive material, a layer of conductive material, a metal, an alloy, copper (Cu), or a material that is know for use as a conductor or a conductive layer in electronic device packages or microprocessor packaging. Layer 306 may be formed by a process, such as is known for forming electroless conductive layers used in electronic device packages. Layer 302 may have thickness TH2 between 5 and 30 microns. In some cases, layer 306 may have thickness TH2 between 10 and 15 microns. Layer 302 may be a metal or conductor, such as copper, gold or aluminum. In some cases, surface 305 may be an insulating substrate surface or electroless conductor (e.g., copper) surface, such as for a chip package.

Layer 304 may be an insulating substrate, a microprocessor packaging substrate, or a substrate having a surface of dielectric, insulator, or ajinomoto build-up film (ABF)). Layer 304 may be or include an insulating substrate, a dielectric material, an electrically insulating material, a polymer material, a polymer material with SiO2 filler, an epoxy with filler (e.g., SiO2), an epoxy without filler, a printed circuit board material, or a material that is known for use as an insulating substrate layer of electronic device packages or use as a layer upon which perform lithographic patterning to form conductive traces (e.g., traces 324 below). Layer 304 may be formed on the top surface of layer 302 by a process, such as is known for forming insulating substrate layers used in electronic device packages or used in lithographic patterning to form conductive traces. Layer 304 may have thickness TH3 between 5 and 30 microns. In some cases, layer 306 may have thickness TH3 between 10 and 15 microns.

FIG. 2A shows a schematic cross-sectional view and profile of unexposed 3D regions of a photo resist layer, and exposed 3D regions of the photo resist layer, having ideal trace quality. FIG. 2A shows schematic cross-sectional profile 200 (e.g., a vertical or Z-height profile) of unexposed 3D regions 314 of a photo resist layer, and exposed 3D regions 312 of the photo resist layer, having ideal trace quality. Areas 312 have width W1 and areas 314 have width W2, such as appropriate for conductive traces formed on the top surface 305 of layer 302. Profile 200 may include ideal (e.g., acceptable) vertical or Z-direction trace quality, borders, or interfaces between regions of light exposed (e.g., cured) and unexposed (e.g., uncured) resist film material.

FIG. 2B shows schematic top profile 201 (e.g., a horizontal or XY profile) of unexposed 3D regions 314 of a photo resist layer, and exposed 3D regions 312 of the photo resist layer, having ideal trace quality. Here, areas 312 and 314 have length L1, such as appropriate for conductive traces formed on the top surface 305 of layer 302. Profile 200 may include ideal (e.g., acceptable) horizontal or XY-direction trace quality, borders, or interfaces between regions of light exposed (e.g., cured) and unexposed (e.g., uncured) resist film material.

FIG. 2C shows a schematic cross-sectional view and profile of unexposed 3D regions of a photo resist layer, and exposed 3D regions of the photo resist layer, having unacceptable borders or defective trace quality (e.g., "border defects"). FIG. 2C shows schematic cross-sectional profile 202 (e.g., a vertical or Z-height profile) of unexposed 3D regions 314 of a photo resist layer, and exposed 3D regions 312 of the photo resist layer, having unacceptable borders or defective trace quality (e.g., "border defects"). Areas 312 have width W1 and areas 314 have width W2, such as appropriate for conductive traces formed on the top surface 305 of layer 302. Profile 202 may include unacceptable vertical or Z-direction trace quality, borders (e.g., "border defects"), or interfaces between regions of light exposed (e.g., cured) and unexposed (e.g., uncured) resist film material.

FIG. 2C shows profile 202 including border B1 having width W4, which is considered an unacceptable vertical or Z-direction trace quality or border (e.g., is a "border defect"). In some cases, W4 is more than 1.0 microns. In some cases, W4 is more than 0.2 microns. In some cases, W4 is more than 0.5 microns.

FIG. 2D shows schematic top profile 203 (e.g., a horizontal or XY profile) of unexposed 3D regions 314 of a photo resist layer, and exposed 3D regions 312 of the photo resist layer, having unacceptable borders or defective trace quality (e.g., "border defects"). Here, areas 312 and 314 have length L1, such as appropriate for conductive traces formed on the top surface 305 of layer 302. Profile 203 may include unacceptable horizontal or XY-direction trace quality, borders (e.g., "border defects"), or interfaces between regions of light exposed (e.g., cured) and unexposed (e.g., uncured) resist film material.

FIG. 2D shows profile 203 including border B2 having width W5, which is considered an unacceptable horizontal or XY-direction trace quality or border (e.g., is a "border defect"). In some cases, W4 is more than 1.0 microns. In some cases, W4 is more than 0.2 microns. In some cases, W4 is more than 0.5 microns.

Examples of unacceptable borders or defective borders (e.g., "border defects") may be or include where one border between two adjacent 3D regions of light exposed (e.g., cured) and unexposed (e.g., uncured) resist film material has a measured, imaged or detected point, pixel, side, part or section that is more than 1.0 microns different (e.g., varied in the X, Y and/or Z direction) from another (e.g., different in the X, Y or Z direction) measured, imaged or detected point, pixel, side, part or section of the same border. In some cases, unacceptable borders or defective borders is more than 0.2 or 0.5 microns different than another.

Understanding the three-dimensional curing profile of dry film photo-resist and solder resist during SPTD lithography process development may be important in-order to achieve tight fine-line spacing, to prevent yield loss due to over/under development of unexposed photo-resist and allow for fundamental understanding of resist polymerization chemistry. Moreover, it may be desired to provide a 3D non-destructive imaging based characterization technique capable of providing in-situ three dimensional chemical information of photo-resist polymerization during SPTD lithography process development. However, resist layer 306 may be optically transparent, and therefore difficult to inspect optically to identify the exposed and unexposed regions, or borders thereof.

According to embodiments, a combined confocal Raman microscope can be used for inspecting layer 306 to detect such border defects between regions of light exposed (e.g., cured) and unexposed (e.g., uncured) resist film material (e.g., as shown in profile 202 or 203). The implementation of the 3D photo-resist chemical imaging and characterization technique using a combined confocal Raman microscope to detect borders between exposed and unexposed photo resist may be based on combining Raman Spectroscopy and confocal imaging. (1) Raman spectroscopy is a spectroscopic technique used to observe vibrational, rotational, and other low-frequency modes in a system (2) Confocal imaging is an optical technique used to increase optical resolution and contrast using point illumination and a spatial pinhole to eliminate out-of-focus light that are thicker than the focal plane. Such use provides a fast high-resolution non-destructive, non-contact in-situ 3D imaging capability that would enable substrate technical design (TD) process to achieve tight fine-line spacing, prevent yield loss due to exposure issues by in-line detection, enable photo-resist material characterization and improve TD velocity and efficiency by enabling robust process optimization.

Figure 3B:
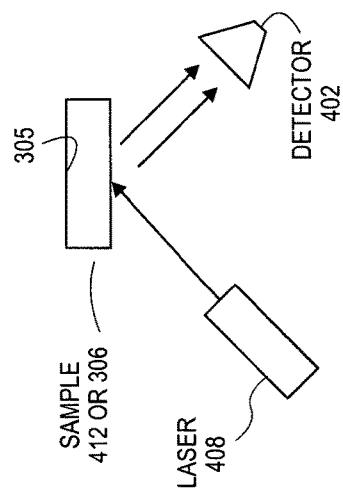
FIG. 3B shows an example of Raman scattering spectrography of a photoresist layer.
Figure 3A:
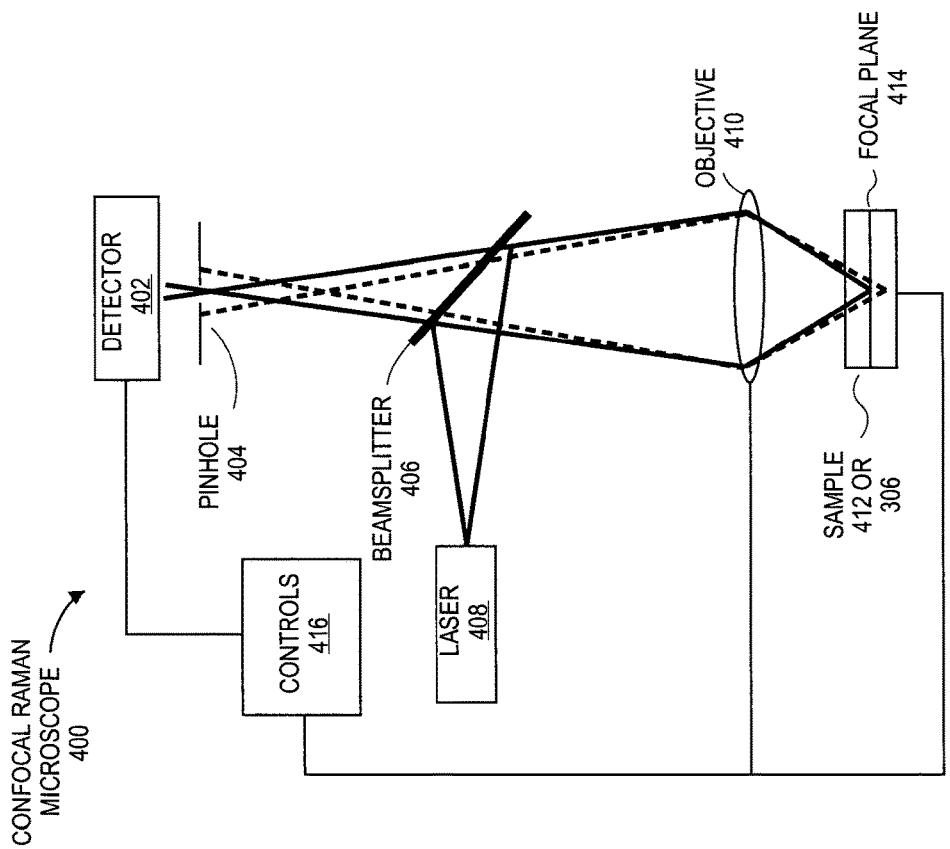
FIG. 3A shows an example of a confocal Raman microscope that may provide a 3D photo-resist chemical imaging and characterization technique.

FIG. 3A shows an example of a confocal Raman microscope that may provide a 3D photo-resist chemical imaging and characterization technique. FIG. 3A shows confocal Raman microscope 400 that may provide a 3D photo-resist chemical imaging and characterization technique of focal plane 414. FIG. 3A shows microscope 400 including detector 402, pinhole 404, beamsplitter 406, laser 408, objective lens 410, sample or layer 306, and focal plane 414. In some cases, sample 412 is layer 306, and focal plane 414 is a vertical or Z-height within thickness TH1 of layer 306. In some cases, a laser 408 emits a Raman beam at a frequency between 400 and 800 (e.g., 785 nm) to detect the 1650 $cm^{-1}$ scattering band; and emits a confocal beam at 1064 nm to select the Z-height (along with adjustment of the focal plane). In some cases, only a single laser device (e.g., able to transmit different frequencies) and single detector is used in the combined device of microscope 400. Controls 416, such as a computer, may be connected to detector 402, objective 410 (such as to move it in the Z direction) and/or a platform upon which substrate 300 or layer 306 is mounted (such as to move layer 306 in the X, Y and Z directions).

FIG. 3B shows an example of Raman scattering spectrography of a photoresist layer. FIG. 3B may shows an example of Raman scattering spectrography of photo resist layer 306 from laser 408 incident upon a top surface of layer 306 through microscope 400. Laser 408 is emitted at frequency V0, but after vibrational modification and reflection from a Z-height within layer 306, returns to detector 402 with two frequencies: (1) V0=the Rayleigh frequency of the material at the spot or pixel of layer 306; and (2) V0 plus and minus VM (vibrational modification and reflection from a Z-height within layer 306)=the Raman frequency of the material at the spot or pixel of layer 306.

For example, the spectral information for the XYZ location of layer 306 being scanned with Raman spectroscopy may be based on the inelastic scattering of monochromatic light (e.g., laser) when the frequency of photons changes upon interaction with a sample. The photons of the laser light are absorbed by the sample and subsequently reemitted. Frequency of the reemitted photons is shifted up or down in comparison with the original monochromatic frequency, which is known as the Raman effect. The Raman shift provides information about vibrational and rotational energies of molecular bonds at the location in layer 306.

In some cases, microscope 400 is a confocal Raman microscope to provide a 3D photo-resist chemical imaging. In some cases, microscope 400 includes laser 408 includes a Raman laser to emit light in a frequency band selected to vibrate C=O bonds in layer 306 to scan an XY plane of the layer of photo resist. In some cases, microscope 400 includes laser 408 includes a confocal laser to emit light in a frequency band to select a Z-height in the layer of photo resist for scanning the XY plane with the Raman laser. In some cases, microscope 400 includes pinhole 404 to receive reflections of the Raman laser and to receive reflections of the confocal laser. In some cases, microscope 400 includes detector 402 configured to chemically identify borders between the exposed regions and unexposed regions of a photo resist layer based on reflections of the Raman laser and of the confocal laser reflected from 3D regions of the photo resist. In some cases, microscope 400 includes detector 402 having a comparator to compare amplitudes of the reflections of the Raman laser to a threshold to identify the borders. In some cases, microscope 400 includes controls 416 to combine XY plane mappings of the identified borders to form a 3D image or map of the borders. In some cases, microscope 400 includes detector 402 having a comparator configured to detect a split in the amplitude of the reflections of the Raman laser in a 1650 cm−1 frequency band.

Figure 3C:
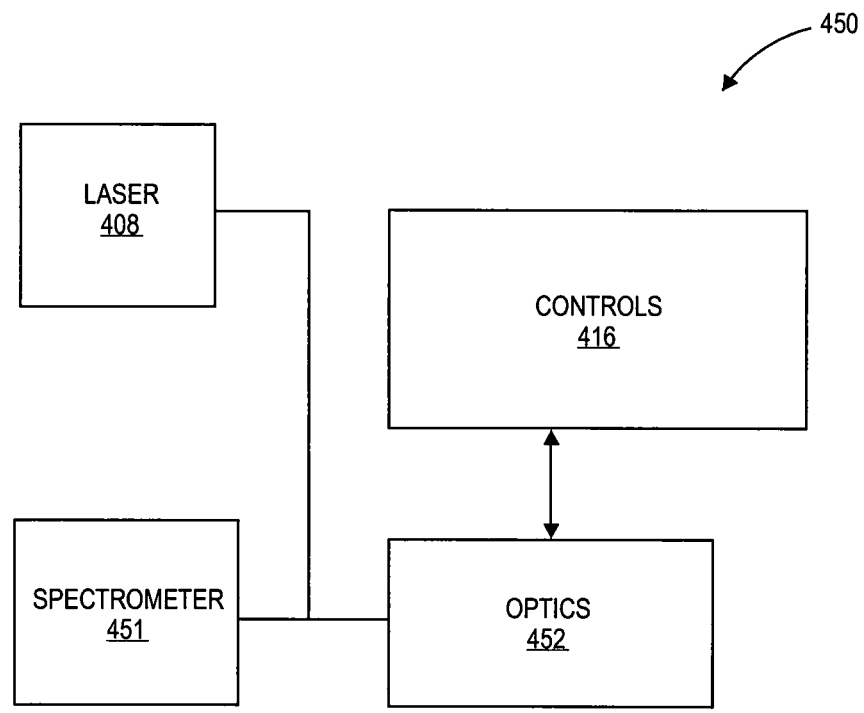
FIG. 3C shows a block diagram of a Raman spectroscopy combined with confocal microscopy device for inspecting the resist.

FIG. 3C shows a block diagram 450 of a Raman spectroscopy combined with confocal microscopy device for inspecting the resist. FIG. 3C may be or include a block diagram of microscope 400 FIG. 3A. FIG. 3C shows a block diagram of laser 408, spectrometer 451 (e.g., which may be or may be part of detector 402), imaging optics 452 (e.g., 404, 406, and 410) and controls 416. Controls 416 may represent computer program instructions as noted below. Controls 416 may represent or include a combination computer program instructions and computer hardware as noted below. Controls 416 may represent or include non-transitory computer program instructions as noted below.

FIG. 3C may show an apparatus setup for 3D chemical imaging of photo-resist in-situ during SPTD lithography process development. The main components may be the confocal 452 and laser 408 modules. Optics 452 to modulate these lasers and a confocal setup to do depth based scanning to generate the 3D image.

According to embodiments, in order to monitor, image, detect, or identify a border between the 3D regions of exposed and unexposed photo resist material (e.g., in layer 306 in 3D) spectrometer 451, laser 408 and optics 452 may include or be changed to include a spectrometer grating arrangement to allow high efficiency Raman signal collection (better than 80 percent thoroughput, or greater than approximatel 80% thoroughput) specific to the photo-resist wavelength modulation region. The laser 408 may include or be changed to include laser wavelengths and power systems specifically optimized for specific photoresist material. The optics 453 may include or be changed to accommodate for polarizers which allow for material anisotropy detection by registering the phase difference between two orthogonally polarized wavespassing through the photoresist material allowing for resolution improvement.

More specifically, in some cases, microscope 400 includes a spectrometer grating configured to allow high efficiency Raman signal collection at a wavelength based on vibrations of C=O bonds in a layer of photo resist. In some cases, microscope 400 includes power systems configured to efficiently provide Raman laser light at a wavelength to produce vibrations of C=O bonds in a layer of photo resist. In some cases, microscope 400 includes polarizers configured to allow for material anisotropy detection by registering a phase difference between two orthogonally polarized waves passing through a layer of photo resist material to allow for improved border resolution.

According to embodiments, confocal Raman microscope 400 may be used to perform photo-resist imaging with chemical specificity by combining Chemistry (Raman Spectroscopy) and 3D-Imaging (Confocal Microscopy) into an integrated apparatus with fast in-line 3D photo-resist imaging and characterization capability. Using microscope 400 provides confocal Raman based 3D chemical imaging or monitoring of the photo-resist polymerization chemistry (e.g., to detect the exposed/unexposed borders of layer 306) in-situ or in-line in 3 dimensions x, y and z by following the vibrational change of C=C double bond to C—C during polymerization of photo-resist. In addition to the C=C change presence of nearby C=O groups close to the reaction center also provides ways to detect the borders. The presence of nearby C=O groups will be detected, imaged or characterized by the shift or disappearance of the 1650 $cm^{-1}$ band in the returned beam Raman scattering spectrography, which would generate a strong Raman shift signal due to population shift of the C=C to C—C (e.g., where the C=C includes and can be identified by a vibration of C=O molecules which are included in the polymer having C=C bonds, by the Raman laser). The chemistry information is provided by the Raman signal while the imaging aspect or depth dependent signal collection is provided by the confocal microscope.

More specifically, the use of confocal Raman microscope 400 to inspect the resist combines the principles of confocal microscopy and Raman spectroscopy. The microscopy allows the laser to be focused in a focal plane at a predetermined or selected Z-height within resist layer 306. Thus, the microscopy can be used to select an X, Y plane at a Z-height, at which to perform the spectroscopy of layer 306. The spectroscopy can be used to identify or detect borders between regions of cured 312 and uncured 314 resistant material layer 306 at the Z-height or along the X, Y plane selected using microscopy. Thus, it is possible to scan (e.g., using a point or fan beam scan Raman scattering spectrography) a selected Z-height of resist material layer 306 to chemically image that Z-plane of material to identify the borders between the cured and uncured material and detect whether they are acceptable or defective. After scanning or imaging an XY plane at one Z-height, a different Z-height, or XY plane at the different Z-height can be selected and mapped in the XY direction as described above.

For example, Raman spectrography scattering can be used to detect the scatter frequency of the laser light received through the confocal microscopy, to detect the vibrational change of a carbon=carbon double bond of exposed or polymerized resist layer 306 (or to detect an adjacent carbon=oxygen double bond for the exposed or polymerized resist), as compared to a carbon—carbon single bond of non-exposed monomer of resist layer 306.

In some embodiments, in addition to the carbon=carbon vibrational change, it has been determined that carbon=oxygen groups or molecules are found close to the reaction center of vibrational changes from carbon=carbon double bond molecules to carbon-carbon single bond molecules at the border between exposed and unexposed resist. The carbon=oxygen groups can be characterized by the shift or disappearance at a frequency of 1650 $cm^{-1}$ scattering band of the Raman reflected laser generates a strong Raman shift (e.g., identifying or detecting the C=O bonds which identify the polymer and allow mapping (e.g., identification or detection)) of where the carbon=carbon double bond forms a border with carbon-carbon single bond, at the border between the exposed and unexposed resist (see FIG. 4). For example, a laser at a frequency between 400 and 800 nm, or at 785 nm can be used to detect the 1650 $cm^{-1}$ scattering band.

In some cases, detector 402 may include a focusing lens, spectrometer (e.g., spectrometer 451 below) and CCD detector. Such a lens may collect a signal from a single point (e.g., pixel) at a Z-height of the resist, disperse it into a spectrum using a spectrometer (e.g., spectrometer 451) and detect the spectrum using a multi-channel detector such as CCD or PDA. In this case, instead of obtaining trivial cumulative information about the spot signal intensity we can obtain a signal spectrum which can be transformed into detailed information about the chemical composition of the given spot on a sample. In other words, we can differentiate the expose and unexposed material based on information contained in the spectra.

In some embodiments, the collection of spectra taken from multiple XY spots of layer 306 is called a "Data Cube" because for a simple 2D X-Y scan the data is represented by a 3D array (cube) where X and Y dimensions hold spatial coordinates and the Z-dimension stores the spectral information. A 3D spectral scan is represented by a 4D Data Cube which includes three spatial dimensions plus one spectral dimension. The additional spectral dimension in Data Cubes provides a powerful tool for differentiation of internal sample structure. It may be difficult to comprehend dense 3D and 4D arrays of data. Therefore, the reconstructing software handling the Data Cubes should have a potent data mining functionality. The useful information from the multi-dimensional data structures may be extracted by slicing them along any of spatial or spectral coordinates.

Figure 4A:
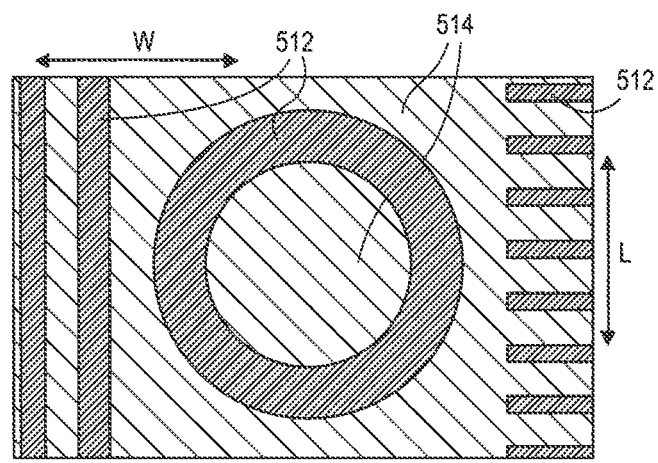
FIG. 4A show a schematic top view of an image of unexposed 3D regions of a photo resist layer, and exposed 3D regions of the photo resist layer. Image FIG. 4B show a schematic cross-sectional or side view of an image of unexposed 3D regions of a photo resist layer, and exposed 3D regions of the photo resist layer.

FIG. 4A show a schematic top view 520 of an image of unexposed 3D regions of a photo resist layer, and exposed 3D regions of the photo resist layer. Image 520 shows horizontal or XY-direction images of exposed 3D regions 512 of a photo resist layer (such as for regions 312), and images of unexposed 3D regions 514 of a photo resist layer (such as for regions 314).

Figure 4B:
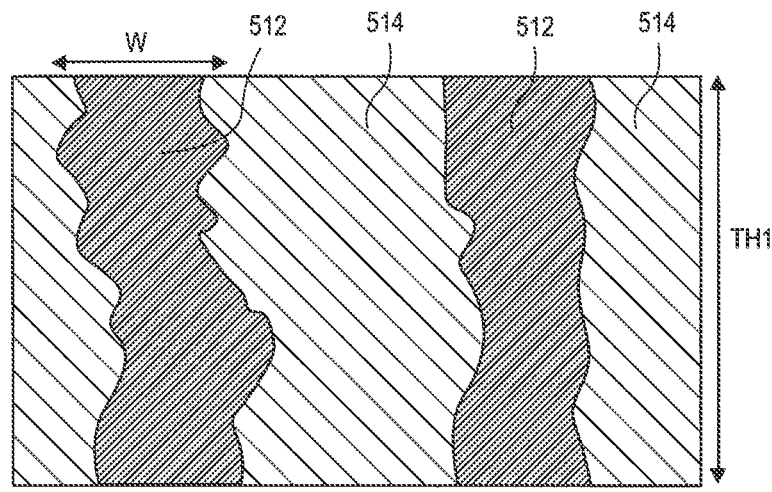
FIG. 4C shows the Raman scattering at the selected Z-height across various band frequencies.

FIG. 4B show a schematic cross-sectional or side view 530 of an image of unexposed 3D regions of a photo resist layer, and exposed 3D regions of the photo resist layer. Image 530 shows vertical or Z-direction images of exposed 3D regions 512 of a photo resist layer (such as for regions 312), and images of unexposed 3D regions 514 of a photo resist layer (such as for regions 314).

In some embodiments, using microscope 400 provide mapping this change in chemical state in xy direction and using confocal optics to get depth information the overall 3D chemical image (e.g., such as images of FIGS. 4A-B) can be obtained. Here, since the photo-resist is homogenously optically transparent any optical method fails to distinguish between the exposed (cured) and unexposed (uncured) photo-resist material. One way to image the exposure photoresist to distinguish cured/uncured regions is to use the underlying chemical specificity of the polymeric reaction that takes place during the litho exposure process. In case of SPTD process build up C═C monomers changing to C—C. Exploiting this using the Raman methodology we can create 3D images showing cured (polymeric) and uncured (monomeric) regions as shown in FIGS. 4A-B, the regions 512 correspond to the cured polymeric state of the photo-resist after exposure.

Figure 4C:
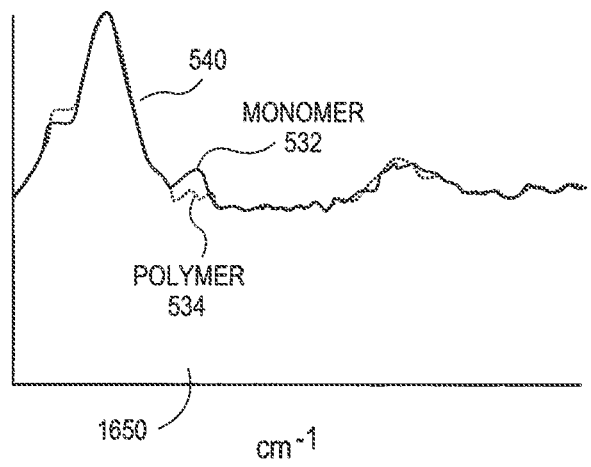

FIG. 4C shows the Raman scattering at the selected Z-height across various band frequencies. FIG. 4C show plot 540 of the Raman scattering of unexposed monomer photo resist 532, and of unexposed monomer photo resist 534. At the 1650 cm$^{-1}$ scattering band frequency there is a difference between the spectrum produced for the carbon double bond and carbon single bond due to the existence of the carbon oxygen double bond. Consequently, this band can be mapped, imaged or monitored to detect or identify the border (e.g., at a point or pixel in 3D) between exposed and unexposed material of layer 306. In some cases, detection of a spike in amplitude at this frequency identifies a border between the exposed and unexposed material, in 3D.

In some cases, the carbon, carbon double bond of the exposed resist absorbs more of the laser light during Ramam spectrography scattering measurements, while the carbon single bond of the unexposed resist absorbs less light and vibrates less. Thus they vibrate with different frequencies. The difference in these frequencies shown where the two bands split at locations to the left and right of the large peak of plot 540 in FIG. 4C. Moreover, notably, the large amplitude split a 1650 cm$^{-1}$ scattering band frequency to the right of the peak in FIG. 4C appears at the vibration frequency of the carbon oxygen double bond group. For example, a laser at a frequency between 400 and 800 nm, or at 785 nm can be used to detect the 1650 cm$^{-1}$ scattering band.

More particularly, FIG. 4C shows a split in the amplitude of reflected Raman laser at the 1650 cm-1 band. The amplitude of reflected Raman laser at the 1650 cm-1 band that is reflected by C═O bonds (e.g. molecule) of the polymer (exposed resist) absorbs more of the Raman laser and provides a lower reflection amplitude 534 than the reflection of the Raman laser from the monomer 532 (unexposed resist). Thus, this lower amplitude reflection can be compared (e.g., by detector 402) to the monomer (unexposed resist) reflection which does not have C═O bonds and does not absorb more of the Raman laser and provides a higher reflection amplitude. Such a comparison may include selecting a threshold amplitude in the scatter frequency band and comparing the reflected or scattered Raman laser amplitude to the threshold to determine if it is (1) above the threshold (e.g., identifying or detecting unexposed monomer resist), or is (2) below the threshold (e.g., identifying or detecting exposed polymer resist).

Using this comparison, and XY image or mapping (e.g., XY profile) of the exposed and unexposed resist can be provided at a certain Z-height (e.g., See FIG. 4A), such as selected by using the confocal aspect (e.g., laser frequency and pinhole) of microscope 400. Subsequently, a different Z-height can be selected using the confocal aspect of microscope 400, and then, using the comparison, a second XY image or mapping of the exposed and unexposed resist can be provided at the different Z-height. The maps at the first and different (as well as other selected) Z-heights can be combined or overlayed (such as by controls 416) to form a Z-height profile (e.g., See FIG. 4B) and/or a 3D image or map of the exposed and unexposed resist.

In some cases, the split in amplitude 532 versus 534 of the Raman laser reflected by the resist (e.g., at an XYZ pixel) at the 1650 cm-1 band is due to selecting a proper frequency for the incident Raman laser to vibrate the C═O bonds or molecule which exists in the polymer, exposed, cured 3D regions (e.g., when reflecting of that laser). These polymer regions also have C═C bonds or molecules due to being polymer. However, in some cases, it is not the C═C bonds or molecules that are identified by the different Raman reflection at the 1650 amplitude split frequency. Instead, C═O bonds or molecule (e.g., is a marker for the polymer because it) does not exist in the monomer, unexposed, uncured 3D regions, so the returned laser from those regions is greater in amplitude.

In some cases, 1650 cm-1 frequency band may be a band that is between 1630 cm-1 and 1660 cm-1 in frequency of the Raman laser reflection or scattering. In some cases, 1650 cm-1 frequency band may be a band that is between 1620 cm-1 and 1670 cm-1 in frequency of the Raman laser reflection or scattering. In some cases, the amplitude difference of the Raman laser reflection is between 5 and 15 percent of the maximum amplitude of the Raman laser reflection or scattering. In some cases, the amplitude difference of the Raman laser reflection is between 10 and 20 percent of the maximum amplitude of the Raman laser reflection or scattering. Thus, the images or mapping (e.g., See FIGS. 4A-B) show 3D step changes across the XY and Z directions at the 1650 freq indicating presence or vacancy of the C═O bonds.

Thus, processes, devices and systems are described for using a combined confocal Raman microscope to provide a 3D photo-resist chemical imaging of a photo resist film formed on the top surface of a layer of a substrate package, to detect border defects between regions of exposed and unexposed photo resist. In some cases, such processes, devices and systems may be implemented in circuitry or hardware located within microscope 400 or controls 416, within a computing device as described herein. Such implementations may include hardware circuitry (e.g., transistors, logic, traces, etc), software, or a combination thereof to perform the processes and functions; and include the devices as described herein.

According to some embodiments, using a combined confocal Raman microscope to provide a 3D photo-resist chemical imaging of a photo resist, or controller 416, includes or may be embodied within a computer program stored in a storage medium, such as a non-transitory or a tangible storage medium. Such a computer program (e.g., program instructions) may be stored in a machine (e.g. computer) readable non-volatile storage medium or memory, such as, a type of disk including floppy disks, optical disks, CD-ROMs, and magnetic-optical disks, read-only memories (ROMs), erasable programmable ROMs (EPROMs), electrically erasable programmable ROMs (EE-PROMs), magnetic or optical cards, magnetic disk storage media, optical storage media, flash memory devices, or any type of media suitable for storing electronic instructions. The processor may be coupled to a storage medium to execute the stored instructions. The processor may also be coupled to a volatile memory (e.g., RAM) into which the instructions are loaded from the storage memory (e.g., non-volatile memory) during execution by the processor. The processor and memory(s) may be coupled to microscope 400 as described herein. In some cases, the processor may perform the functions of controls 416. The processor may be controlled by the computer program (e.g., program instructions), such as those stored in the machine readable non-volatile storage medium.

Use of a confocal Raman microscope may provide a 3D photo-resist chemical imaging and characterization technique (e.g., see FIGS. 3-4) based on combining (1) Raman spectroscopy to identify, map or detect the border between regions of light exposed and unexposed resist film along horizontal or XY planes, with (2) Confocal imaging to select a vertical height or Z-height for the XY planes scanned with Raman spectroscopy. Such use of a confocal Raman microscope may provide 3D photoresist chemical imaging, with fast, high resolution imaging to distinguish trace quality in a process that is non-destructive to the resist. Such detection provides fast, high resolution, non-destructive in-line inspection, and improves technical development (TD) of polymerization profiles of the resist film material. In some cases, use of the embodiments improving TD including the process and design of the mask, light, resist, and the like described for block 106 and FIG. 1B.

The confocal Raman microscope may provide a 3D photo-resist chemical imaging and characterization technique based on combining (1) Raman spectroscopy to identify, map or detect the border between regions of light exposed and unexposed resist film along horizontal or XY planes, with (2) Confocal imaging to select a vertical height or Z-height for the XY planes scanned with Raman spectroscopy.

Embodiments include devices, systems and processes for using a combined confocal Raman microscope to provide a 3D photo-resist chemical imaging of a photo resist film formed on the top surface of a layer of a substrate package, to detect border defects between regions of light exposed (e.g., cured) and unexposed (e.g., uncured) resist film material. Use of the confocal Raman microscope may provide a 3D photo-resist chemical imaging and characterization technique based on combining (1) Raman spectroscopy to identify the borders between regions of light exposed and unexposed resist along XY planes, with (2) Confocal imaging to select a Z-height of the XY planes scanned. Such detection provides fast, high resolution, non-destructive in-line inspection, and improves technical development of polymerization profiles of the resist film material.

Embodiments described herein can be used to inspect photo resist formed on substrates, such as substrates used to form a microprocessor package, a "chip" package, or a printed circuit board during "in-line" processing, such as processing that does not require the substrate to be removed from a fabrication process where the substrate, or chips diced from the substrate will be manufacture for inclusion in a product; or such as without requiring the substrate to be taken from processing or tested in a laboratory (e.g. by dissection or a process that damages or causes the substrate to be unusable for sale or inclusion in a product). For example, in-line monitoring may include monitoring fabrication of devices that are sold to the public or are included in a device sold to the public. In-line monitoring may include monitoring manufacturing flow of a device or package, such as by adding the processes or embodiments described herein into the manufacturing flow, concluding manufacturing of the device, and selling the device or including the device in a product. Such in-line monitoring may occur at or after block 106 or 126; FIG. 3 and/or 4. Thus, embodiments described herein provide devices and processes for using a combined confocal Raman microscope to provide a 3D photo-resist chemical imaging of a photo resist to provide a high-throughput and low cost tool for non-destructive, non-contact in-line monitoring of resist to detect exposed photo resist region and unexposed resist photo region border defects (e.g., FIG. 2C-D).

Embodiments described herein may be used to inspect or detect to detect exposed photo resist region and unexposed resist photo region border defects in package wafers or diced insulating substrate packages, such as a substrate used in of an electronic device package, a microprocessor package, or a substrate having a surface of dielectric, insulator, or ajinomoto build-up film (ABF). Such substrate may be package substrates upon which a processor or microprocessor will be mounted. Such a packages, wafers or substrates may include through silicon vias (TSV). Such packages may be for packaging logic or memory TSV wafers. In some cases, the packages may be for packaging CPUs, chipsets, graphics chips, or other high density logic device that want to implement 3D stacking (TSV).

Figure 5:
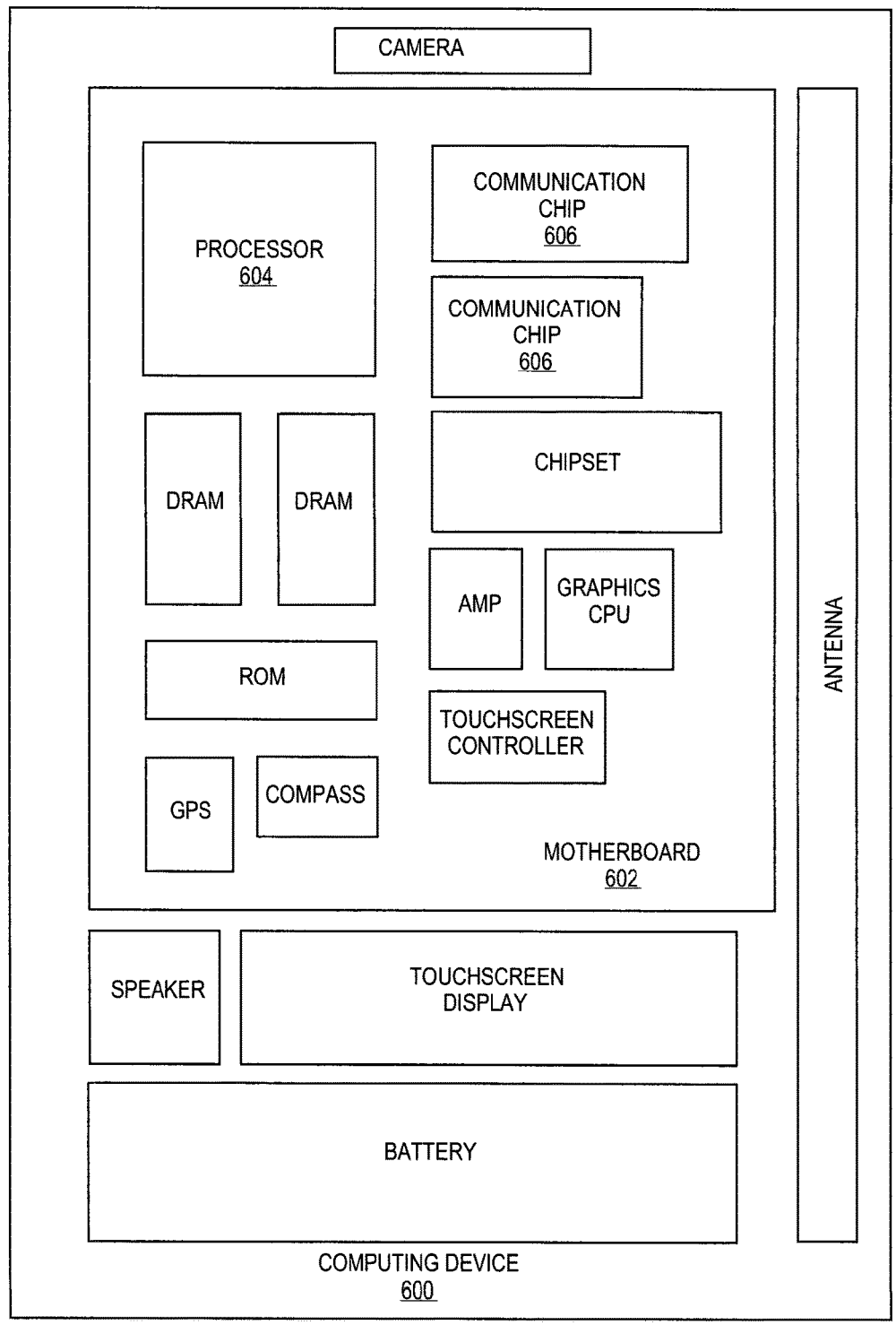
FIG. 5 illustrates a computing device, such as a system on a chip (SoC), in accordance with some implementations.

FIG. 5 illustrates a computing device 600, such as a system on a chip (SoC), in accordance with some implementations. The computing device 600 houses board 602. Board 602 may include a number of components, including but not limited to processor 604 and at least one communication chip 606. Processor 604 is physically and electrically connected to board 602, such as using or through a processor package which may include substrate 300, or a packaging substrate which may have been inspected using embodiments of a combined confocal Raman microscope to provide a 3D photo-resist chemical imaging of a photo resist to detect exposed photo resist region and unexposed resist photo region border defects, as noted herein. In some implementations at least one communication chip 606 is also physically and electrically connected to board 602, such as using or through a processor package which may include substrate 300, or a packaging substrate which may have been inspected using embodiments of a combined confocal Raman microscope to provide a 3D photo-resist chemical imaging of a photo resist to detect exposed photo resist region and unexposed resist photo region border defects, as noted herein. In further implementations, communication chip 606 is part of processor 604.

In some cases, FIG. 5 illustrates a computing device 600 including a system on a chip (SoC) 602, in accordance with one implementation. In some cases, FIG. 6 shows an example of a Systems on a chip (SoC) technology (e.g., motherboard 602). Such a SoC may include a microprocessor or CPU, as well as various other components, including electronics and transistors for power and battery regulation; radio frequency (RF) processing, receipt and transmission; voltage regulation; power management; and possibly other systems such as those that may be found in a cellular telephone, etc. FIG. 5 may include one or more additional processors or chips mounted on board 602 or on another component such as a different card or PCB, such as using or through a processor package which may include substrate 300, or a packaging substrate which may have been inspected using embodiments of a combined confocal Raman microscope to provide a 3D photo-resist chemical imaging of a photo resist to detect exposed photo resist region and unexposed resist photo region border defects, as noted herein.

Depending on its applications, computing device 600 may include other components that may or may not be physically and electrically connected to board 602. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth).

Communication chip 606 enables wireless communications for the transfer of data to and from computing device 600. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. Communication chip 606 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. Computing device 600 may include a plurality of communication chips 606. For instance, a first communication chip 606 may be dedicated to shorter range wireless communications such as Wi-Fi and Bluetooth and a second communication chip 606 may be dedicated to longer range wireless communications such as GPS, EDGE, GPRS, CDMA, WiMAX, LTE, Ev-DO, and others.

Processor 604 of computing device 600 includes an integrated circuit die packaged within processor 604. In some implementations, the integrated circuit die is packaged within, using or through a processor package which may include substrate 300, or a packaging substrate which may have been inspected using embodiments of a combined confocal Raman microscope to provide a 3D photo-resist chemical imaging of a photo resist to detect exposed photo resist region and unexposed resist photo region border defects, as noted herein, thus providing more stable and solidly bonded conductive traces on a packaging substrate, as noted herein, such as with reference to FIGS. 1-4. The term "processor" may refer to any device or portion of a device that processes electronic data from registers and/or memory to transform that electronic data into other electronic data that may be stored in registers and/or memory. In some cases, processor 604 may be a SoC.

Communication chip 606 also includes an integrated circuit die packaged within communication chip 606. In some implementations, this integrated circuit die is packaged within, using or through a processor package which may include substrate 300, or a packaging substrate which may have been inspected using embodiments of a combined confocal Raman microscope to provide a 3D photo-resist chemical imaging of a photo resist to detect exposed photo resist region and unexposed resist photo region border defects, as noted herein, thus providing more stable and solidly bonded conductive traces on a packaging substrate, as noted herein, such as with reference to FIGS. 1-4.

In various implementations, computing device 600 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, computing device 600 may be any other electronic device that processes data.

EXAMPLES

The following examples pertain to embodiments.

Example 1 is a method for detecting defects in an border between exposed regions of a photo resist layer and unexposed regions of the photo resist layer comprising: inspecting the layer of photo resist with a confocal Raman microscope, wherein the resist is formed a conductive surface and includes borders between exposed regions of the photo resist layer and unexposed regions of the photo resist layer, wherein inspecting includes chemically identifing the borders between the exposed regions and unexposed regions.

In Example 2, the subject matter of Example 1 can optionally include, further comprising, prior to inspecting, exposing a layer of photo resist formed on a conductive surface to light to form borders between exposed regions of the photo resist layer and unexposed regions of the photo resist layer.

In Example 3, the subject matter of Example 1 can optionally include, further comprising, indentifying acceptable and unacceptable borders or trace quality based on the chemically identifed borders.

In Example 4, the subject matter of Example 1 can optionally include, wherein inspecting includes, inspecting a first XY plane of the layer of photo resist at a first Z-height of the photo resist to form a first XY plane mapping of the borders based on the chemically identified borders.

In Example 5, the subject matter of Example 4 can optionally include, further comprising selecting the first Z-height of the photo resist using a confocal laser frequency and pinhole of microscope.

In Example 6, the subject matter of Example 4 can optionally include, further comprising inspecting a second XY plane of the layer of photo resist at a second Z-height of the photo resist to form a second XY plane mapping of the borders based on the chemically identified borders.

In Example 7, the subject matter of Example 6 can optionally include, further comprising combining the first and second XY plane mappings of the borders to form a 3D image or map of the borders.

In Example 8, the subject matter of Example 4 can optionally include, wherein inspecting an XY plane includes inspecting by reflecting a Raman laser along the first XY plane, and wherein a Z-height of the photo resist is selected using a confocal laser and pinhole.

In Example 9, the subject matter of Example 1 can optionally include, further comprising selecting a frequency of a Raman laser of the microscope to vibrate C=O bonds in the exposed regions.

In Example 10, the subject matter of Example 9 can optionally include, further comprising detecting a split in the amplitude of reflected Raman laser at a 1650 cm−1 frequency band, wherein detecting includes comparing Raman laser light reflected by the layer of resist with a threshold to detect a difference in amplitude in a frequency band selected based on vibration of C=O bonds in the layer of resist.

Example 11 is a confocal Raman microscope to provide a 3D photo-resist chemical imaging comprising: a Raman laser to emit light in a frequency band selected to vibrate C=O bonds in the layer of photo resist to scan an XY plane of the layer of photo resist; a confocal laser to emit light in a frequency band to select a Z-height in the layer of photo resist for scanning the XY plane with the Raman laser; a pinhole to receive reflections of the Raman laser and to receive reflections of the confocal laser; and a detector configured to chemically identify borders between the exposed regions and unexposed regions of a photo resist layer based on reflections of the Raman laser and of the confocal laser reflected from 3D regions of the photo resist.

In Example 12, the subject matter of Example 11 can optionally include, further comprising a comparator to compare amplitudes of the reflections of the Raman laser to a threshold to identify the borders.

In Example 13, the subject matter of Example 11 can optionally include, wherein the detector is configured to detect a split in the amplitude of the reflections of the Raman laser in a 1650 cm−1 frequency band.

In Example 14, the subject matter of Example 13 can optionally include, further comprising a spectrometer grating configured to allow high efficiency Raman signal collection at a wavelength based on vibrations of C=O bonds in a layer of photo resist.

In Example 15, the subject matter of Example 13 can optionally include, further comprising power systems configured to efficiently provide Raman laser light at a wavelength to produce vibrations of C=O bonds in a layer of photo resist.

In Example 16, the subject matter of Example 13 can optionally include, further comprising polarizers configured to allow for material anisotropy detection by registering a phase difference between two orthogonally polarized waves passing through a layer of photo resist material to allow for improved border resolution.

In Example 17, the subject matter of Example 13 can optionally include, further comprising a controller to combine XY plane mappings of the identified borders to form a 3D image or map of the borders.

Example 18 is a non-transitory computer-readable medium storing data and instructions to cause a programmable processor to perform operations comprising detecting defects in an border between exposed regions of a photo resist layer and unexposed regions of the photo resist layer comprising, wherein detecting: inspecting the layer of photo resist with a confocal Raman microscope, wherein the resist is formed a conductive surface and includes borders between exposed regions of the photo resist layer and unexposed regions of the photo resist layer, wherein inspecting includes chemically identifying the borders between the exposed regions and unexposed regions.

In Example 19, the subject matter of Example 18 can optionally include, further comprising instructions for indentifying acceptable and unacceptable borders or trace quality based on the chemically identified borders.

In Example 20, the subject matter of Example 18 can optionally include, wherein inspecting includes, inspecting a first XY plane of the layer of photo resist at a first Z-height of the photo resist to form a first XY plane mapping of the borders based on the chemically identified borders.

In Example 21, the subject matter of Example 20 can optionally include, further comprising instructions for selecting the first Z-height of the photo resist using a confocal laser frequency and pinhole of microscope.

In Example 22, the subject matter of Example 20 can optionally include, further comprising instructions for inspecting a second XY plane of the layer of photo resist at a second Z-height of the photo resist to form a second XY plane mapping of the borders based on the chemically identified borders.

In Example 23, the subject matter of Example 22 can optionally include, further comprising instructions for comprising combining the first and second XY plane mappings of the borders to form a 3D image or map of the borders.

In Example 24, the subject matter of Example 18 can optionally include, further comprising instructions for selecting a frequency of a Raman laser of the microscope to vibrate C=O bonds in the exposed regions.

It should also be appreciated that reference throughout this specification to "one embodiment", "an embodiment", "one or more embodiments", or "different embodiments", for example, means that a particular feature may be included in the practice of the embodiments. Similarly, it should be appreciated that in the description various features are sometimes grouped together in a single embodiment, figure, or description thereof for the purpose of streamlining the disclosure and aiding in the understanding of various inventive aspects of embodiments. This method of disclosure, however, is not to be interpreted as reflecting an embodiment that requires more features than are expressly recited in each claim. Rather, as the following claims reflect, inventive aspects of embodiments that may lie in less than all features of a single disclosed embodiment. For example, although the descriptions and figures above describe using a combined confocal Raman microscope for inspecting a photo resist film material layer formed on the top surface of a layer of a substrate package, it may be possible to include using a combined confocal Raman microscope in a system with a platform to hold the substrate, but without the substrate itself (e.g., such as a system to be sold to or used by others). Thus, the claims following the Detailed Description are hereby expressly incorporated into this Detailed Description, with each claim standing on its own as a separate embodiment of the invention.

What is claimed is:

1. A method for detecting defects in a border between exposed regions of a photo resist layer and unexposed regions of the photo resist layer comprising:

inspecting the layer of photo resist with a confocal Raman microscope, wherein the photo resist layer is formed directly on a conductive surface and includes borders between exposed regions of the photo resist layer and unexposed regions of the photo resist layer, wherein inspecting includes chemically identifying the borders between the exposed regions and unexposed regions of the photo resist layer;

selecting a frequency of a Raman laser of the microscope to vibrate C=O bonds in the exposed regions; and detecting a split in the amplitude of reflected Raman laser at a 1650 cm-1 frequency band wherein detecting includes comparing Raman laser light reflected by the layer of resist with a threshold to detect a difference in amplitude in a frequency band selected based on vibration of C=O bonds in the layer of resist.

2. The method of claim 1, further comprising, prior to inspecting, exposing a photo resist layer formed on the conductive surface to light to form the borders between exposed regions of the photo resist layer and unexposed regions of the photo resist layer.

3. The method of claim 1, further comprising identifying acceptable and unacceptable borders or trace quality based on the chemically identified borders.

4. The method of claim 1, wherein inspecting includes, inspecting a first XY plane of the layer of photo resist at a first Z-height of the photo resist to form a first XY plane mapping of the borders based on the chemically identified borders.

5. The method of claim 4, further comprising selecting the first Z-height of the photo resist using a confocal laser frequency and pinhole of microscope.

6. The method of claim 4, further comprising inspecting a second XY plane of the layer of photo resist at a second Z-height of the photo resist to form a second XY plane mapping of the borders based on the chemically identified borders.

7. The method of claim 6, further comprising combining the first and second XY plane mappings of the borders to form a 3D image or map of the borders.

8. The method of claim 4, wherein inspecting an XY plane includes inspecting by reflecting a Raman laser along the first XY plane, and wherein a Z-height of the photo resist is selected using a confocal laser and pinhole.

9. The method of claim 1 wherein a wavelength of a Raman laser of the microscope is between 400 and 800 nm, and where in wherein a wavelength of confocal light of the microscope is approximately 1064 nm.

10. A confocal Raman microscope to provide a 3D photo-resist chemical imaging comprising:

a Raman laser to emit light in a frequency band selected to vibrate C=O bonds in a layer of photo resist to scan an XY plane of the layer of photo resist;

a confocal laser to emit light in a frequency band to select a Z-height in the layer of photo resist for scanning the XY plane with the Raman laser;

a pinhole to receive reflections of the Raman laser and to receive reflections of the confocal laser; and a detector configured to chemically identify borders between the exposed regions and unexposed regions of the layer of photo resist based on reflections of the Raman laser and of the confocal laser reflected from 3D regions of the layer of photo resist formed directly upon a conductive surface, wherein the detector is configured to detect a split in the amplitude of the reflections of the Raman laser at frequencies comprising at least a 1650 cm-1 frequency band.

11. The microscope of claim 10, further comprising a comparator to compare amplitudes of the reflections of the Raman laser to a threshold to identify the borders.

12. The microscope of claim 10, further comprising a spectrometer grating configured to allow high efficiency Raman signal collection at a wavelength based on vibrations of C=O bonds in a layer of photo resist.

13. The microscope of claim 10, further comprising power systems configured to efficiently provide Raman laser light at a wavelength to produce vibrations of C=O bonds in a layer of photo resist.

14. The microscope of claim 10, further comprising a controller to combine XY plane mappings of the identified borders to form a 3D image or map of the borders.

15. The microscope of claim 10, wherein a wavelength of a Raman laser of the microscope is between 400 and 800 nm, and where in wherein a wavelength of confocal light of the microscope is approximately 1064 nm.

16. A confocal Raman microscope to provide a 3D photo-resist chemical imaging comprising:

a Raman laser to emit light in a frequency band selected to vibrate C=O bonds in a layer of photo resist to scan an XY plane of the layer of photo resist;

a confocal laser to emit light in a frequency band to select a Z-height in the layer of photo resist for scanning the XY plane with the Raman laser;

a pinhole to receive reflections of the Raman laser and to receive reflections of the confocal laser;

a detector configured to chemically identify borders between the exposed regions and unexposed regions of the layer of photo resist based on reflections of the Raman laser and of the confocal laser reflected from 3D regions of the layer of photo resist formed directly upon a conductive surface; and polarizers configured to allow for material anisotropy detection by registering a phase difference between two orthogonally polarized waves passing through a layer of photo resist material to allow for improved border resolution.

17. A non-transitory computer-readable medium storing data and instructions to cause a programmable processor to perform operations comprising detecting defects in a border between exposed regions of a photo resist layer and unexposed regions of the photo resist layer, wherein detecting comprises:

inspecting the layer of the photo resist layer with a confocal Raman microscope, wherein the photo resist layer is formed directly on a conductive surface and includes borders between exposed regions of the photo resist layer and unexposed regions of the photo resist layer, wherein inspecting includes chemically identifying the borders between the exposed regions and unexposed regions of the photo resist layer; and the non-transitory computer-readable medium further comprising:

instructions for detecting a split in the amplitude of a reflected Raman laser of the confocal Raman microscope at frequencies comprising at least a 1650 cm-1 frequency band.

18. The medium of claim 17, further comprising instructions for identifying acceptable and unacceptable borders or trace quality based on the chemically identified borders.

19. The medium of claim 17, wherein inspecting includes, inspecting a first XY plane of the layer of photo resist at a first Z-height of the photo resist to form a first XY plane mapping of the borders based on the chemically identified borders.

20. The medium of claim 19, further comprising instructions for selecting the first Z-height of the photo resist using a confocal laser frequency and pinhole of microscope.

21. The medium of claim 19, further comprising instructions for inspecting a second XY plane of the layer of photo resist at a second Z-height of the photo resist to form a second XY plane mapping of the borders based on the chemically identified borders.

22. The medium of claim 21, further comprising instructions for combining the first and second XY plane mappings of the borders to form a 3D image or map of the borders.

23. The medium of claim 17, further comprising instructions for selecting a frequency of a Raman laser of the microscope to vibrate C=O bonds in the exposed regions.

24. The medium of claim 17, wherein a wavelength of a Raman laser of the microscope is between 400 and 800 nm, and wherein a wavelength of confocal light of the microscope is approximately 1064 nm.

25. A method for detecting defects in a border between exposed regions of a photo resist layer and unexposed regions of the photo resist layer comprising:
inspecting the layer of photo resist with a confocal Raman microscope, wherein the photo resist layer is formed directly on a conductive surface and includes borders between exposed regions of the photo resist layer and unexposed regions of the photo resist layer, wherein inspecting includes chemically identifying the borders between the exposed regions and unexposed regions of the photo resist layer; and detecting a split in the amplitude of a reflected Raman laser of the confocal Raman microscope at frequencies comprising at least a 1650 cm-1 frequency band.

26. A method for detecting defects in a border between exposed regions of a photo resist layer and unexposed regions of the photo resist layer comprising:
inspecting the layer of photo resist with a confocal Raman microscope, wherein the photo resist layer is formed directly on a conductive surface and includes borders between exposed regions of the photo resist layer and unexposed regions of the photo resist layer, wherein inspecting includes chemically identifying the borders between the exposed regions and unexposed regions of the photo resist layer, wherein chemically identifying includes comparing Raman laser light reflected by the layer of resist with a threshold to detect a difference in amplitude in a frequency band selected based on vibration of C=O bonds in the layer of resist.

27. A confocal Raman microscope to provide a 3D photo-resist chemical imaging comprising:
a Raman laser to emit light in a frequency band selected to vibrate C=O bonds in a layer of photo resist to scan an XY plane of the layer of photo resist;
a confocal laser to emit light in a frequency band to select a Z-height in the layer of photo resist for scanning the XY plane with the Raman laser;
a pinhole to receive reflections of the Raman laser and to receive reflections of the confocal laser; and
a detector configured to chemically identify borders between the exposed regions and unexposed regions of the layer of photo resist based on reflections of the Raman laser and of the confocal laser reflected from 3D regions of the layer of photo resist formed directly upon a conductive surface, wherein chemically identifying includes comparing Raman laser light reflected by the layer of resist with a threshold to detect a difference in amplitude and a frequency band selected based on vibration of C=O bonds in the layer of resist.

28. A non-transitory computer-readable medium storing data and instructions to cause a programmable processor to perform operations comprising detecting defects in a border between exposed regions of a photo resist layer and unexposed regions of the photo resist layer, wherein detecting comprises:
inspecting the layer of the photo resist layer with a confocal Raman microscope, wherein the photo resist layer is formed directly on a conductive surface and includes borders between exposed regions of the photo resist layer and unexposed regions of the photo resist layer, wherein inspecting includes chemically identifying the borders between the exposed regions and unexposed regions of the photo resist layer, wherein chemically identifying includes comparing Raman laser light reflected by the layer of resist with a threshold to detect a difference in amplitude and a frequency band selected based on vibration of C=O bonds in the layer of resist.

29. A method for detecting defects in a border between exposed regions of a photo resist layer and unexposed regions of the photo resist layer comprising:
inspecting the layer of photo resist with a confocal Raman microscope, wherein the photo resist layer is formed on a conductive surface and includes borders between exposed regions of the photo resist layer and unexposed regions of the photo resist layer, wherein inspecting includes chemically identifying the borders between the exposed regions and unexposed regions of the photo resist layer;
selecting a frequency of a Raman laser of the microscope to vibrate C=O bonds in the exposed regions; and
detecting a split in the amplitude of reflected Raman laser at a 1650 cm-1 frequency band wherein detecting includes comparing Raman laser light reflected by the layer of resist with a threshold to detect a difference in amplitude in a frequency band selected based on vibration of C=O bonds in the layer of resist.

30. A confocal Raman microscope to provide a 3D photo-resist chemical imaging comprising:
a Raman laser to emit light in a frequency band selected to vibrate C=O bonds in a layer of photo resist to scan an XY plane of the layer of photo resist;
a confocal laser to emit light in a frequency band to select a Z-height in the layer of photo resist for scanning the XY plane with the Raman laser;
a pinhole to receive reflections of the Raman laser and to receive reflections of the confocal laser; and
a detector configured to chemically identify borders between the exposed regions and unexposed regions of the layer of photo resist based on reflections of the Raman laser and of the confocal laser reflected from 3D regions of the layer of photo resist, wherein the detector is configured to detect a split in the amplitude of the reflections of the Raman laser at frequencies comprising at least a 1650 cm-1 frequency band.

31. A confocal Raman microscope to provide a 3D photo-resist chemical imaging comprising:
a Raman laser to emit light in a frequency band selected to vibrate C=O bonds
in a layer of photo resist to scan and XY plane of the layer of photo resist;
a confocal laser to emit light in a frequency band to select a Z-height in the layer of photo resist for scanning the XY plane with the Raman laser;
a pinhole to receive reflections of the Raman laser and to receive reflections of the confocal laser;
a detector configured to chemically identify borders between the exposed regions and unexposed regions of the layer of photo resist based on reflections of the Raman laser and of the confocal laser reflected from 3D regions of the layer of photo resist, and polarizers configured to allow for material anisotropy detection by registering a phase difference between two orthogonally polarized waves passing through a layer of photo resist material allow for improved border resolution.

32. A non-transitory computer-readable medium storing data and instructions to cause a programmable processor to perform operations comprising detecting defects in a border between exposed regions of a photo resist layer and unexposed regions of the photo resist layer, wherein detecting comprises:

inspecting the layer of the photo resist layer with a confocal Raman microscope, wherein the photo resist layer is formed on a conductive surface and includes borders between exposed regions of the photo resist layer and unexposed regions of the photo resist layer, wherein inspecting includes chemically identifying the borders between the exposed regions and unexposed regions of the photo resist layer, further comprising instructions for detecting a split in the amplitude of a reflected Raman laser of the confocal Raman microscope at frequencies comprising at least a 1650 cm-1 frequency band.

33. A method for detecting defects in a border between exposed regions of a photo resist layer and unexposed regions of the photo resist layer comprising:

inspecting the layer of photo resist with a confocal Raman microscope, wherein the photo resist layer is formed on a conductive surface and includes borders between exposed regions of the photo resist layer and unexposed regions of the photo resist layer, wherein inspecting includes chemically identifying the borders between the exposed regions and unexposed regions of the photo resist layer; and detecting a split in the amplitude of a reflected Raman laser of the confocal Raman microscope at frequencies comprising at least a 1650 cm-1 frequency band.

34. A method for detecting defects in a border between exposed regions of a photo resist layer and unexposed regions of the photo resist layer comprising:

inspecting the layer of photo resist with a confocal Raman microscope, wherein the photo resist layer is formed on a conductive surface and includes borders between exposed regions of the photo resist layer and unexposed regions of the photo resist layer, wherein inspecting includes chemically identifying the borders between the exposed regions and unexposed regions of the photo resist layer, wherein chemically identifying includes comparing Raman laser light reflected by the layer of resist with a threshold to detect a difference in amplitude in a frequency band selected based on vibration of C=O bonds in the layer of resist.

35. A confocal Raman microscope to provide a 3D photo-resist chemical imaging comprising:

a Raman laser to emit light in a frequency band selected to vibrate C=O bonds in a layer of photo resist to scan an XY plane of the layer of photo resist;

a confocal laser to emit light in a frequency band to select a Z-height in the layer of photo resist for scanning the XY plane with the Raman laser;

a pinhole to receive reflections of the Raman laser and to receive reflections of the confocal laser; and a detector configured to chemically identify borders between the exposed regions and unexposed regions of the layer of photo resist based on reflections of the Raman laser and of the confocal laser reflected from 3D regions of the layer of photo resist, wherein chemically identifying includes comparing Raman laser light reflected by the layer of resist with a threshold to detect a difference in amplitude and a frequency band selected based on vibration of C=O bonds in the layer of resist.

36. A non-transitory computer-readable medium storing data and instructions to cause a programmable processor to perform operations comprising detecting defects in a border between exposed regions of a photo resist layer and unexposed regions of the photo resist layer, wherein detecting comprises:

inspecting the layer of the photo resist layer with a confocal Raman microscope, wherein the photo resist layer is formed on a conductive surface and includes borders between exposed regions of the photo resist layer and unexposed regions of the photo resist layer, wherein inspecting includes chemically identifying the borders between the exposed regions and unexposed regions of the photo resist layer, wherein chemically identifying includes comparing Raman laser light reflected by the layer of resist with a threshold to detect a difference in amplitude and a frequency band selected based on vibration of C=O bonds in the layer of resist.

* * * * *